(12) United States Patent
Kalkstein et al.

(10) Patent No.: US 12,020,783 B2
(45) Date of Patent: *Jun. 25, 2024

(54) METHODS AND SYSTEMS OF EVALUATING A RISK OF LUNG CANCER

(71) Applicant: Medial Research Ltd., Kfar Malal (IL)

(72) Inventors: Nir Kalkstein, Herzlia (IL); Yaron Kinar, Tel-Aviv (IL); Varda Shalev, RaAnana (IL); Gabriel Chodick, Givataim (IL); Inbal Goldshtein, Ramat-HaSharon (IL)

(73) Assignee: Medial Research Ltd., Kfar Malal (IL)

( * ) Notice: Subject to any disclaimer, the term of this patent is extended or adjusted under 35 U.S.C. 154(b) by 463 days.

This patent is subject to a terminal disclaimer.

(21) Appl. No.: 17/340,137

(22) Filed: Jun. 7, 2021

(65) Prior Publication Data
US 2021/0295960 A1 Sep. 23, 2021

Related U.S. Application Data

(63) Continuation of application No. 15/035,232, filed as application No. PCT/IL2014/050960 on Nov. 5, 2014, now Pat. No. 11,031,105.
(Continued)

(51) Int. Cl.
*G16H 10/40* (2018.01)
*G16B 20/00* (2019.01)
(Continued)

(52) U.S. Cl.
CPC ............. *G16H 10/40* (2018.01); *G16B 20/00* (2019.02); *G16H 50/20* (2018.01); *G16H 50/30* (2018.01); *G16H 10/60* (2018.01)

(58) Field of Classification Search
CPC ........ G16H 10/40; G16H 50/20; G16H 50/30; G16H 10/60; G16B 20/00; A61B 5/14532;
(Continued)

(56) References Cited

U.S. PATENT DOCUMENTS 4,733,354 A 3/1988 Potter et al.
5,687,716 A * 11/1997 Kaufmann ............. G16H 50/20
706/924
(Continued)

FOREIGN PATENT DOCUMENTS

CN 1268033 9/2000
CN 101180408 5/2008
(Continued)

OTHER PUBLICATIONS

John K. Field et al., International Association for the Study of Lung Cancer Computed Tomography Screening Workshop 2011 Report, Journal of Thoracic Oncology,vol. 7, Issue 1, Jan. 2012 (Year: 2012).*

(Continued)

*Primary Examiner* — Joshua B Blanchette

(57) ABSTRACT

A method of evaluating lung cancer risk by generating a set of features comprising a plurality of current blood test results from a blood collected from a target individual, providing at least one classifier generated according to an analysis of a plurality of respective historical blood test results of each of another of a plurality of sampled individuals, and evaluating, using a processor, a lung cancer risk of said target individual by classifying said set of features using said at least one classifier. Each of said plurality of historical and current blood test results comprises results of one or more selected blood tests such as white blood cells blood test results, biochemistry test results, platelets blood test results including at least one of platelets count and mean platelet volume (MPV) and/or a combination of smoking history and red cell test results.

22 Claims, 2 Drawing Sheets

Related U.S. Application Data

(60) Provisional application No. 61/901,059, filed on Nov. 7, 2013.

(51) Int. Cl.
    *G16H 10/60*     (2018.01)
    *G16H 50/20*     (2018.01)
    *G16H 50/30*     (2018.01)

(58) Field of Classification Search
CPC . A61B 5/14542; A61B 5/1455; A61B 5/4842; A61B 5/08; A61B 5/145; G01N 33/49
See application file for complete search history.

(56) References Cited

U.S. PATENT DOCUMENTS

| | | | | |
|---|---|---|---|---|
| 6,059,724 | A * | 5/2000 | Campell | G16H 50/50 |
| | | | | 128/923 |
| 2003/0065535 | A1* | 4/2003 | Karlov | G16H 50/20 |
| | | | | 705/2 |
| 2007/0118399 | A1 | 5/2007 | Avinash et al. | |
| 2007/0178504 | A1 | 8/2007 | Colpitts et al. | |
| 2008/0160546 | A1 | 7/2008 | Colpitts et al. | |
| 2010/0070191 | A1* | 3/2010 | Gold | G01N 33/57423 |
| | | | | 436/64 |
| 2010/0179067 | A1 | 7/2010 | Patz, Jr. et al. | |
| 2010/0248290 | A1 | 9/2010 | Lam et al. | |
| 2012/0101002 | A1 | 4/2012 | Riel-Mehan et al. | |
| 2012/0128702 | A1 | 5/2012 | Weinschenk et al. | |
| 2016/0292379 | A1 | 10/2016 | Kalkstein et al. | |

FOREIGN PATENT DOCUMENTS

| | | |
|---|---|---|
| EP | 1969363 | 9/2008 |
| EP | 2518507 | 10/2012 |
| JP | 2001-511680 | 8/2001 |
| JP | 2009-521692 | 6/2009 |
| JP | 2010-528265 | 8/2010 |
| JP | 2012-502281 | 1/2012 |
| WO | WO 96/12187 | 4/1996 |
| WO | WO 98/35609 | 8/1998 |
| WO | WO 2007/076439 | 7/2007 |
| WO | WO 2008/144034 | 11/2008 |
| WO | WO 2009/065230 | 5/2009 |
| WO | WO 2010/030697 | 3/2010 |
| WO | WO 2013/048292 | 4/2013 |
| WO | WO 2015/068157 | 5/2015 |

OTHER PUBLICATIONS

Spitz "A Risk Model for Prediction of Lung Cancer," J Natl Cancer Inst 2007 (Year: 2007).*
Barger TE, Zhou L, Hale M, Moxness M, Swanson SJ, Chirmule N. Comparing exponentially weighted moving average and run rules in process control of semiquantitative immunogenicity immunoassays. AAPS J. Mar. 2010;12(1):79-86. doi: 10.1208/s12248-009-9166-4. Epub Dec. 10, 2009. (Year: 2010).*
O. González-Recio, J.A. Jiménez-Montero, R. Alenda, The gradient boosting algorithm and random boosting for genome-assisted evaluation in large data sets,Journal of Dairy Science, vol. 96, Issue 1, 2013, pp. 614-624 (Year: 2013).*
Advisory Action Before the Filing of an Appeal Brief dated Jun. 11, 2019 From the US Patent and Trademark Office Re. U.S. Appl. No. 15/035,232. (12 Pages).
Advisory Official Action dated Oct. 14, 2020 From the US Patent and Trademark Office Re. U.S. Appl. No. 15/035,232. (6 Pages).
Communication Pursuant to Article 94(3) EPC dated Feb. 11, 2019 From the European Patent Office Re. Application No. 14859375.9. (7 Pages).
Communication Pursuant to Article 94(3) EPC dated Aug. 27, 2019 From the European Patent Office Re. Application No. 14859375.9. (7 Pages).
Decision to Grant dated Nov. 14, 2018 From the ROSPatent, Federal Service for Intellectual Property, Patents and Trademarks of the Russian Federation Re. Application No. 2016121682 and Its Translation of Office Action Into English. (20 Pages).
Examination Report dated Nov. 5, 2019 From the Australian Government, IP Australia Re. Application No. 2014347669. (5 Pages).
Examination Report dated Nov. 19, 2020 From the Instituto Mexicano de la Propiedad Industrial, Direccion Divisional de Patentes Re. Application No. MX/a/2016/005825 and Its Machine Translation Into English. (5 Pages).
Examination Report Under Sections 12 & 13 of the Patents Act, 1970 and the Patents Rules, 2003 dated Sep. 29, 2020 From the Government of India, Intellectual Property India, Patents, Designs, Trade Marks, Geographical Indications, The Patent Office Re. Application No. 201627018716. (7 Pages).
Final Official Action dated Jun. 19, 2020 from the US Patent and Trademark Office Re. U.S. Appl. No. 15/035,232. (26 pages).
Ground(s) of Reason of Rejection dated Jan. 21, 2021 From the Korean Intellectual Property Office Re. Application No. 10-2016-7014533 and Its Translation Into English. (5 Pages).
International Preliminary Report on Patentability dated May 19, 2016 From the International Bureau of WIPO Re. Application No. PCT/IL2014/050960.
International Search Report and the Written Opinion dated Mar. 11, 2015 From the International Searching Authority Re. Application No. PCT/IL2014/050960.
Interview Summary dated Aug. 4, 2020 From the US Patent and Trademark Office Re. U.S. Appl. No. 15/035,232. (3 Pages).
Notice of Allowance dated Mar. 3, 2021 From the US Patent and Trademark Office Re. U.S. Appl. No. 15/035,232. (16 Pages).
Notice of Reasons for Rejection dated May 7, 2019 From the Japan Patent Office Re. Application No. 2016-526346 and Its Translation Into English. (5 Pages).
Notice of Reasons for Rejection dated Aug. 14, 2018 From the Japan Patent Office Re. Application No. 2016-526346 and Its Translation Into English. (8 Pages).
Notification of Office Action and Search Report dated Jan. 2, 2018 From the State Intellectual Property Office of the People's Republic of China Re. Application No. 201480067921.8. (8 Pages).
Notification of Office Action and Search Report dated Aug. 15, 2018 From the State Intellectual Property Office of the People's Republic of China Re. Application No. 201480067921.8 and Its Summary in English. (9 Pages).
Notification of Office Action dated Apr. 1, 2019 From the State Intellectual Property Office of the People's Republic of China Re. Application No. 201480067921.8. (7 Pages).
Office Action dated Nov. 20, 2019 From the Israel Patent Office Re. Application No. 245515 and Its Translation Into English. (5 Pages).
Official Action dated Dec. 11, 2019 From the US Patent and Trademark Office Re. U.S. Appl. No. 15/035,232. (27 pages).
Official Action dated Jan. 24, 2019 From the US Patent and Trademark Office Re. U.S. Appl. No. 15/035,232. (24 pages).
Official Action dated May 29, 2018 From the US Patent and Trademark Office Re. U.S. Appl. No. 15/035,232. (27 pages).
Patent Examination Report dated Nov. 14, 2018 From the Australian Government, IP Australia Re. Application No. 2014347669. (.6 Pages).
Re-Examination Report dated Sep. 7, 2020 From the Australian Government, IP Australia Re. Application No. 2014347669. (4 Pages).
Re-Examination Report dated Jun. 9, 2020 From the Australian Government, IP Australia Re. Application No. 2014347669. (.5 Pages).
Request for Examination and Search Report dated Jun. 21, 2018 From the Federal Government Institution, Federal Institute of Industrial Property of the Federal Service for Intellectual Property, Patents and Trademarks of the Russian Federation Re. Application No. 2016121682 and Its Translation of Office Action Into English. (17 Pages).
Requisition dated Dec. 15, 2020 From the Innovation, Science and Economic Development Canada, Canadian Intellectual Property Office Re. Application No. 2,928,271. (5 Pages).

(56) References Cited

OTHER PUBLICATIONS

Search Report and Opinion dated Aug. 13, 2020 From the Servico Publico Federal, Ministerio da Economia, Instituto Nacional da Propriedade Industrial do Brasil Re. Application No. BR112016010322-0 and Its Translation Into English. (8 Pages).
Supplementary European Search Report and the European Search Opinion dated Jun. 19, 2017 From the European Patent Office Re. Application No. 14859375.9. (11 Pages).
Translation Dated Sep. 5, 2018 of Notification of Office Action dated Aug. 15, 2018 From the State Intellectual Property Office of the People's Republic of China Re. Application No. 201480067921.8. (5 Pages).
Translation Dated Apr. 9, 2019 of Notification of Office Action dated Apr. 1, 2019 From the State Intellectual Property Office of the People's Republic of China Re. Application No. 201480067921.8. (6 Pages).
Translation Dated Jul. 15, 2018 of Search Report dated Jun. 21, 2018 From the Federal Government Institution, Federal Institute of Industrial Property of the Federal Service for Intellectual Property, Patents and Trademarks of the Russian Federation Re. Application No. 2016121682.
Translation of Notification of Office Action and Search Report dated Jan. 2, 2018 From the State Intellectual Property Office of the People's Republic of China Re. Application No. 201480067921.8. (4 Pages).
Gonzalez Barcala et al. "Platelet Count: Association With Prognosis in Lung Cancer", Medical Oncology, XP055375583, 27(2): 357-362, Published Online Apr. 21, 2009. Abstract.
Sarraf et al. "Neutrophil/Lymphocyte Ratio and Its Association With Survival After Complete Resection in Non-Small Cell Lung Cancer", The Journal of Thoracic and Cardiovascular Surgery, XP025892189, 137(2): 425-428, Feb. 28, 2009. Abstract.
Spitz et al. "A Risk Model for Prediction of Lung Cancer", JNCI: Journal of the National Cancer Institute, 99(9), 715-726, May 2, 2007, May 2, 2007.

\* cited by examiner

METHODS AND SYSTEMS OF EVALUATING A RISK OF LUNG CANCER

RELATED APPLICATION/S

This application is a continuation of U.S. patent application Ser. No. 15/035,232, filed on May 8, 2016, which is a National Phase of PCT Patent Application No. PCT/IL2014/050960 having International Filing Date of Nov. 5, 2014, which claims the benefit of priority under 35 USC § 119(e) of U.S. Provisional Patent Application No. 61/901,059 filed on Nov. 7, 2013. The contents of the above applications are all incorporated by reference as if fully set forth herein in their entirety.

FIELD AND BACKGROUND OF THE INVENTION

The present invention, in some embodiments thereof, relates to cancer diagnosis and, more particularly, but not exclusively, to methods and systems of evaluating a risk of cancer.

Lung cancer is the leading cause of cancer death worldwide. In addition, lung cancer has one of the lowest survival outcomes of any cancer since over two-thirds of patients are diagnosed at a late stage when curative treatment is not possible. An effective lung cancer screening will lead to earlier detection of the disease (before patients have symptoms and when treatment is more likely to be effective) and will decrease mortality. Currently, most of the lung cancer cases are diagnosed clinically when patients present with symptoms (such as cough, chest pain, weight loss); unfortunately, patients with these symptoms usually have advanced lung cancer.

Until very recently, lung cancer screening programs were rarely practiced worldwide, and early detection of lung cancer occurred sporadically through chest radiography. Recent studies indicated that Low Dose Computed Tomography (LDCT) can be used to screen patients who are at high risk for lung cancer. The National Lung Screening Trial (NLST) compared the use of LDCT and chest radiography for screening 53,454 persons at high risk for lung cancer. The study demonstrated a 20% reduction in mortality from lung cancer with LDCT comparing to chest radiography screening. Following the NLST and additional supporting studies, new guidelines for Lung cancer screening were issued recommending the practice of LDCT based lung cancer screening programs.

Although recommended, lung cancer screening with LDCT has inherited risks: (A) High false positive results, leading to unnecessary testing and invasive procedures, increased costs, and decreased quality of life because of mental anguish. (B) False negative results, which may delay or prevent diagnosis and treatment. (C) Inability to detect small aggressive tumors. (D) Over-diagnosis. (E) Radiation exposure. Therefore, there is a great need to accurately identify the high risk individuals and prevent potential harm from individuals at lower risk. To this end, lung cancer screening guidelines suggest criteria for determining which patients are at high risk. These criteria are based on a combination of age, smoking history, and additional risk factors. Unfortunately, these criteria fail to accurately identify patients at a treatable cancer stage. In fact, the NLST results indicate that in order to prevent one death from lung cancer (in the US), 320 high risk individuals must be screened with LDCT. The implications of such a relatively low rate should be studied to determine if the benefits are greater than the harms of this screening process. Overall, there is a great need to develop a model that identifies patients at high risk for lung cancer (at the pre-screening stage), and enables an efficient, minimal risk screening program by screening only those individuals with high chance of having cancer.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
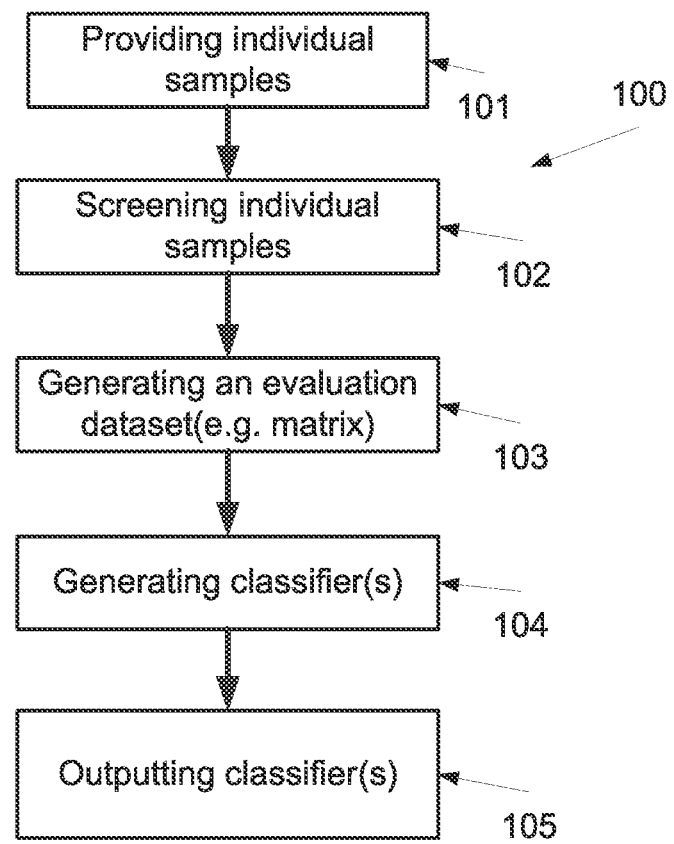
FIG. 1 is a flowchart of a method of generating one or more classifiers for estimating a lung cancer risk score according to an analysis of a plurality of individual records, according to some embodiments of the present invention.

According to some embodiments of the present invention, there is provided a computerized method of evaluating lung cancer risk. The method comprises generating a set of features comprising a plurality of current blood test results from a blood collected from a target individual, providing at least one classifier generated according to an analysis of a plurality of respective historical blood test results of each of another of a plurality of sampled individuals, and evaluating, using a processor, a lung cancer risk of the target individual by classifying the set of features using the at least one classifier. Each of the plurality of historical and current blood test results comprises results of at least one the following blood tests: white blood cells blood test results including at least one of neutrophils count, basophils count, eosinophils count, lymphocytes count, monocytes count, WBC count, neutrophils percentage, basophils percentage, eosinophils percentage, lymphocytes percentage, and monocytes percentage wherein the set of features comprising a plurality of historical blood test results from the blood collected from the target individual, biochemistry test results, platelets blood test results including at least one of platelets count and mean platelet volume (MPV), and a combination of smoking history and red cell test results including at least one of red blood cells (RBC), red cell distribution width (RDW), blood tests hemoglobin (MCH), mean cell volume (MCV), mean corpuscular hemoglobin concentration (MCHC), Hematocrit, and Hemoglobin.

Optionally, the Biochemistry test results is selected from a group consisting of Erythrocyte Sedimentation Rate (ESR), Glucose, Urea, Blood Urea Nitrogen (BUN), Creatinine, Sodium, Potassium, Chloride, Calcium, Phosphorus, Uric Acid, Bilirubin Total, Lactate Dehydrogenase (LDH), glutamic oxaloacetic transaminase (GOT), Serum glutamic oxaloacetic transaminase (SGOT), and Glutamate Oxaloacetate, Aspartate transaminase (AST), Aspartate Aminotransferase, glutamate pirovate transaminase (GPT) Serum glutamate pirovate transaminase (SGPT), alanine aminotransferase (ALT), Alkaline Phosphatase (Alk Phos/ALP), gamma glutamyl transpeptidase (GGT), Albumin, CK (Creatine Kinase), Iron, HbA1, B12, Vitamin D, G-6-PD, Lithium, Folic Acid, CRP (C reactive protein), low-density lipoprotein (LDL), high-density lipoprotein (HDL), Triglycerides, Total cholesterol, Amylase, PT (Prothrombin Time), Partial Thromboplastin Time (PTT), Activated Partial Thromboplastin Time (APPT), (International Normalized Ratio (INR), Fibrinogen, Cytidine triphosphate (CPT), Ferritin, glomerular filtration rate (GFR), transferrin, Total iron-binding capacity (TIBC), Unsaturated iron-binding capacity (UIBC).

Optionally, the at least one classifier being generated according to a combination of the plurality of historical and current blood test results and at least one demographic parameter of each of the plurality of sampled individuals.

More optionally, the at least one demographic parameter is a member of a group consisting of gender, age, residential zone, race and socio-economic characteristic.

Optionally, each of the plurality of historical and current blood test results comprises results of white blood cells blood test results including at least one of neutrophils count, basophils count, eosinophils count, lymphocytes count, monocytes count, WBC count, neutrophils percentage, basophils percentage, eosinophils percentage, lymphocytes percentage, monocytes percentage.

More optionally, each of the plurality of historical and current blood test results comprises smoking history.

Optionally, each of the plurality of historical and current blood test results comprises platelets blood test results including at least one of platelets count and MPV.

More optionally, each of the plurality of historical and current blood test results comprises smoking history.

More optionally, each of the plurality of historical and current blood test results comprises smoking history.

Optionally, each of the plurality of historical and current blood test results comprises the combination of smoking history and red cell test results including at least one of RBC, RDW, MCH, MCV, MCHC, Hematocrit, and Hemoglobin.

Optionally, each of the plurality of historical and current blood test results comprises results of both neutrophils percentage/count and lymphocytes percentage/count.

Optionally, the at least one classifier comprises a member of a group consisting of: a weighted linear regression classifier, a K-Nearest neighbors (KNN) classifier, and a random forest classifier.

Optionally, each of the plurality of historical and current blood test results comprises results of Platelets hematocrit (PCT).

Optionally, each of the plurality of historical and current blood test results comprises results of both HGB and HCT.

Optionally, the set of features comprises an age of the target individual; wherein the at least one classifier is generated according to an analysis of the age of each of another of a plurality of sampled individuals.

Optionally, each of the plurality of historical and current blood test results comprises at least one of the following blood tests: eosinophils count; neutrophils percentage; monocytes percentage; eosinophils percentage; basophils percentage; and neutrophils count; monocytes count.

Optionally, the set of features comprises an age of the target individual; wherein the at least one classifier is generated according to an analysis of the age of each of another of a plurality of sampled individuals.

Optionally, each of the plurality of historical and current blood test results comprises results of red cell distribution width (RDW).

Optionally, each of the plurality of historical and current blood test results comprises Biochemistry test results selected from Erythrocyte Sedimentation Rate (ESR), Glucose, Urea, Blood Urea Nitrogen (BUN), Creatinine, Sodium, Potassium, Chloride, Calcium, Phosphorus, Uric Acid, Bilirubin Total, Lactate Dehydrogenase (LDH), glutamic oxaloacetic transaminase (GOT), Serum glutamic oxaloacetic transaminase (SGOT), and Glutamate Oxaloacetate, Aspartate transaminase (AST), Aspartate Aminotransferase, glutamate pirovate transaminase (GPT) Serum glutamate pirovate transaminase (SGPT), alanine aminotransferase (ALT), Alkaline Phosphatase (Alk Phos/ALP), gamma glutamyl transpeptidase (GGT), Albumin, CK (Creatine Kinase), Iron, HbA1, B12, Vitamin D, G-6-PD, Lithium, Folic Acid, CRP (C reactive protein), low-density lipoprotein (LDL), high-density lipoprotein (HDL), Triglycerides, Total cholesterol, Amylase, PT (Prothrombin Time), Partial Thromboplastin Time (PTT), Activated Partial Thromboplastin Time (APPT), (International Normalized Ratio (INR), Fibrinogen, Cytidine triphosphate (CPT), Ferritin, glomerular filtration rate (GFR), transferrin, Total iron-binding capacity (TIBC), Unsaturated iron-binding capacity (UIBC).

Optionally, each of the plurality of historical and current blood test results comprises results of Platelets hematocrit (PCT).

Optionally, each of the plurality of historical and current blood test results comprises results of mean cell volume (MCV).

Optionally, each of the plurality of historical and current blood test results comprises at least one of the following blood tests: white blood cell count—WBC (CBC); mean platelet volume (MPV); mean cell; platelet count (CBC); eosinophils count; neutrophils percentage; monocytes percentage; eosinophils percentage; basophils percentage; and neutrophils count; monocytes count.

Optionally, the at least one classifier comprises a member of a group consisting of: a weighted linear regression classifier, a K-Nearest neighbors (KNN) classifier, a gradient boosting machine (GBM) classifier, and a random forest classifier.

Optionally, the set of features comprises at least one demographic characteristic of the target individual and the at least one classifier generated according to an analysis of respective the at least one demographic characteristic of each of the plurality of sampled individuals.

Optionally, the method further comprises selecting the at least one classifier according to at least one demographic characteristic of the individual from a plurality of classifiers each generated according to a plurality of respective historical blood test results of sampled individuals having at least one different demographic characteristic.

Optionally, the plurality of blood test results comprises at least one result from the following plurality of blood tests: biochemistry test results may include any of the following blood test results Albumin, Calcium, Chloride, Cholesterol, Creatinine, high density lipoprotein (HDL), low density lipoprotein (LDL), Potassium, Sodium, Triglycerides, Urea, and/or Uric Acid.

According to some embodiments of the present invention, there is provided a lung cancer evaluating system. The system comprises a processor, a memory unit which stores at least one classifier generated according to an analysis of a plurality of historical blood test results of each of another of a plurality of sampled individuals, an input unit which receives a plurality of current blood test results taken from a blood of a target individual, and a lung cancer evaluating module which evaluates, using the processor, a lung cancer risk of the target individual by classifying, using the at least one classifier, a set of features extracted from the plurality of current blood test results. Each of the plurality of historical and current blood test results comprises results of at least one the following blood tests: white blood cells blood test results including at least one of neutrophils count, basophils count, eosinophils count, lymphocytes count, monocytes count, WBC count, neutrophils percentage, basophils percentage, eosinophils percentage, lymphocytes percentage, monocytes percentage; wherein the set of features comprising a plurality of historical blood test results from the blood collected from the target individual, biochemistry test results, and, platelets blood test results including at least one of platelets count and mean platelet volume (MPV), and a combination of smoking history and red cell test results including at least one of red blood cells (RBC), red cell distribution width (RDW), blood tests hemoglobin (MCH), mean cell volume (MCV), mean corpuscular hemoglobin concentration (MCHC), Hematocrit, and Hemoglobin.

Optionally, each of the plurality of historical and current blood test results comprises results of red cell distribution width (RDW).

Optionally, each of the plurality of historical and current blood test results comprises results of Platelets hematocrit (PCT).

Optionally, each of the plurality of historical and current blood test results comprises of mean cell volume (MCV).

According to some embodiments of the present invention, there is provided a method of generating a classifier for a lung cancer risk evaluation. The method comprises providing a plurality of historical blood test results of each of another of a plurality of sampled individuals, generating a dataset having a plurality of sets of features each set generated according to respective plurality of historical blood test results of another the plurality of sampled individuals, generating at least one classifier for a lung cancer risk evaluation according to an analysis the dataset and outputting the at least one classifier.

Optionally, the generating comprises calculating and adding at least one manipulated version of an historical blood test result taken from a respective the plurality of historical blood test results as a feature to respective the set of features.

Optionally, the generating comprises weighting each the set of features according to a date of the respective plurality of historical blood test results.

Optionally, the generating comprises filtering the plurality of sets of features to remove outliers according to a standard deviation maximum threshold.

Optionally, the plurality of sets of features are weighted according to a date of the respective plurality of historical blood test results.

Optionally, the plurality of blood test results of at least one the following blood tests: red blood cells (RBC), hemoglobin (HGB), and hematocrit (HCT) and at least one result of the following blood tests hemoglobin (MCH) and mean corpuscular hemoglobin concentration (MCHC).

Optionally, each of the plurality of historical and current blood test results comprises results of red cell distribution width (RDW).

Optionally, each of the plurality of historical and current blood test results comprises results of Platelets hematocrit (PCT).

Optionally, each of the plurality of historical and current blood test results comprises results of mean cell volume (MCV).

More optionally, the method further comprises adding at least one demographic parameter of each of the plurality of sampled individuals to a respective the set of features.

More optionally, the at least one demographic parameter is a member of a group consisting of gender, age, residential zone, race and socio-economic characteristic.

More optionally, the generating comprises calculating and adding at least one manipulated version of the at least one demographic parameter as a feature to respective the set of features.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

According to some embodiments of the present invention, there are provided methods and systems of evaluating lung cancer risk by classifying a set of current blood test results of a target individual using one or more classifiers which are generated according to an analysis of historical blood test results of a plurality of individuals.

Reference is now made to FIG. 1, which is a flowchart of a method 100 of generating one or more classifiers for estimating a lung cancer risk score according to an analysis of a plurality of historical test results of each of a plurality of diagnosed individuals, according to some embodiments of the present invention.

Figure 2:
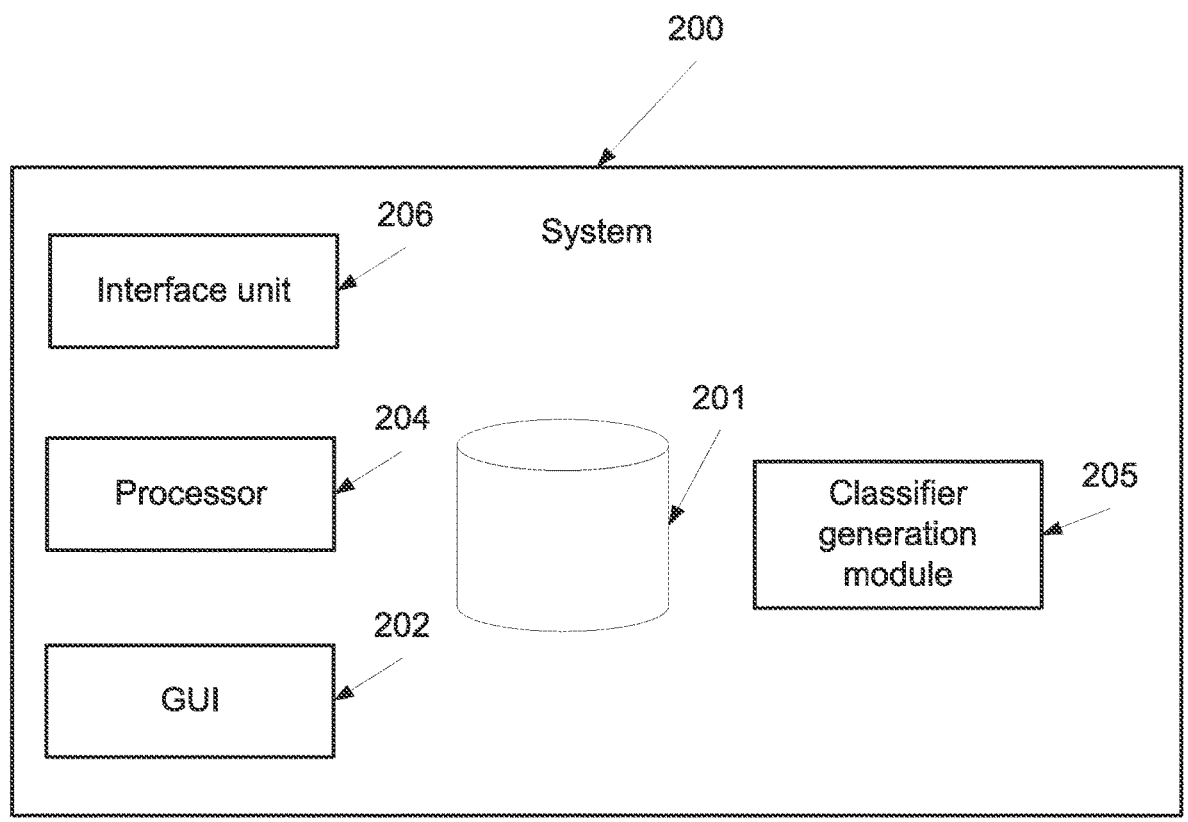
FIG. 2 is a schematic illustration of a system for generating one or more classifiers, for example by implementing the method depicted in FIG. 1, according to some embodiments of the present invention.

Reference is also made to FIG. 2, which is a schematic illustration of a system 200 for generating classifier(s) for estimating lung cancer risk scores, for example by implementing the method depicted in FIG. 1, according to some embodiments of the present invention.

The system 200 includes to one or more medical record database(s) 201 and/or connected to a medical record database interface. The database(s) 201 include a plurality of individual records, also referred to as a plurality of individual samples, which describe, for each of another of a plurality of sampled individuals, one or more sets of a plurality of historical test results each set of another individual, and optionally one or more demographic parameter(s) and a lung cancer diagnosis The set of a plurality of historical test results, demographic parameter(s), such as age, and/or lung cancer prognosis may be stored in a common sample record and/or gathered from a number of independent and/or connected databases. Optionally, the lung cancer prognosis is a binary indication set according to a cancer registry record. The different test results may be of commonly performed blood tests biochemistry tests and/or blood tests held during the same period. Optionally, some sets of a plurality of historical test results have missing blood test results. These results are optionally completed by weighted averaging of the available blood test results of other individuals. The method further includes a processor 204, a classifier generation module 205, and an interface unit 206, such as a network interface.

As used herein, a demographic parameter includes age, gender, race, weight, national origin, geographical region of residence and/or the like.

First, as shown at 101, one or more dataset(s) of a plurality of individual samples are provided.

Optionally, as shown at 102, the plurality of individual samples are screened and/or selected according to matching criteria. For example, the sample records are of individuals in the age of 30 or older who either appear in a cancer registry with lung cancer, and optionally without other types of cancer, or do not appear in the cancer registry. Optionally, sample records of individuals that appear in the cancer registry are taken only if the latest set of a plurality of historical test results they document was taken during a certain period before the registration of a respective individual in the cancer registry, for example during a period of at least 30 days before a current date and at most 2 years. Optionally, sample records of individuals that do not appear in the cancer registry are taken only if they include a set of a plurality of historical test results that creates an equal time-distribution (blood tests timing) for the positive and negative lung cancer populations. The process of equating the time-distribution of the positive and negative samples also leads to omit at least some negative (non-registered) samples and to a change in the lung cancer prevalence in the data set.

Now, as shown at 103, a derivation dataset, such as a matrix, is generated according to the sample data extracted from the sample records, for example by the classifier generation module 205. The derivation dataset includes a plurality of sets of features, optionally expended. Each set of features is generated from each one of the screened and/or selected sample records. The set of features are optionally unprocessed features which includes actual blood test and/or demographic characteristic values.

Each sample record includes one or more sets of a plurality of historical test results of a individual, each includes a combination blood test results and/or biochemistry test results, for example a combination of more than 10, 15, 20 and/or any intermediate number of blood test results or less. In one example, each extracted set of unprocessed features includes at least the following 18 blood test results: red blood cells (RBC); white blood cell count—WBC (CBC); mean platelet volume (MPV); hemoglobin (HGB); hematocrit (HCT); mean cell volume (MCV); mean cell hemoglobin (MCH); mean corpuscular hemoglobin concentration (MCHC); red cell distribution width (RDW); platelet count (CBC); eosinophils count; neutrophils percentage; monocytes percentage; eosinophils percentage; basophils percentage; neutrophils count; monocytes count; and Platelets hematocrit (PCT). Optionally, this extracted set of unprocessed features further includes one or more of the following blood tests RDW, Platelets, and MCV. Additionally, this extracted set of unprocessed features may further includes one or more of the following blood tests WBC, eosinophils count, neutrophils percentage and/or count, basophils percentage and/or count, and monocytes percentage and/or count.

The set of current blood test results includes some or more of the following Biochemistry test results: Erythrocyte Sedimentation Rate (ESR), Glucose, Urea, Blood Urea Nitrogen (BUN), Creatinine, Sodium, Potassium, Chloride, Calcium, Phosphorus, Uric Acid, Bilirubin Total, Lactate Dehydrogenase (LDH), glutamic oxaloacetic transaminase (GOT), Serum glutamic oxaloacetic transaminase (SGOT), and Glutamate Oxaloacetate, Aspartate transaminase (AST), Aspartate Aminotransferase, glutamate pirovate transaminase (GPT) Serum glutamate pirovate transaminase (SGPT), alanine aminotransferase (ALT), Alkaline Phosphatase (Alk Phos/ALP), gamma glutamyl transpeptidase (GGT), Albumin, CK (Creatine Kinase), Iron, HbA1, B12, Vitamin D, G-6-PD, Lithium, Folic Acid, CRP (C reactive protein), low-density lipoprotein (LDL), high-density lipoprotein (HDL), Triglycerides, Total cholesterol, Amylase, PT (Prothrombin Time), Partial Thromboplastin Time (PTT), Activated Partial Thromboplastin Time (APPT), (International Normalized Ratio (INR), Fibrinogen, Cytidine triphosphate (CPT), Ferritin, glomerular filtration rate (GFR), transferrin, Total iron-binding capacity (TIBC), Unsaturated iron-binding capacity (UIBC).

Optionally, the set of unprocessed features is expended. The expended set of features contains features as the above unprocessed blood test results and/or biochemistry test results and/or smoking data and/or one or more demographic parameter(s) and optionally manipulated blood test results and/or combination of blood test results, for instance as described below. For example, each feature in the set of expended features is based on a blood test result, a demographic characteristic, a smoking history, biochemistry test results, a combination of blood test result(s) and/or demographic characteristic(s), and/or a manipulation of blood test result(s) and/or demographic characteristic(s). For example, when the set of unprocessed features includes 18 test results, an expended set of 95 to 190, for example 114 features may be generated.

Optionally, different derivation datasets, for example matrixes, having different sets of expended features are generated to create different classifiers which classify target individuals having different demographic characteristic(s), for example gender, different smoking history and/or different current data.

Optionally, the derivation dataset, for example the matrix, is filtered, to remove iteratively outliers. Optionally, an average deviation and/or a standard deviation of each feature is calculated and features having exceptional values, for example more than a standard deviation maximum threshold, for example 10, are truncated to the standard deviation maximum threshold. For example, the process is iteratively repeated 10 times (or less if no truncations are performed). Now, as shown at 104, the derivation dataset is used for generating classifier(s) each classifying a lung cancer risk of a target individual based on one or more demographic characteristics thereof and a current set of a plurality of test results, for example by the classifier generation module 205. Optionally, one or more of the following classifiers may be generated based on the derivation dataset:

a weighted linear regression classifier where positive sample records receive a score that is about 100 times the score of negative sample records;
   a K-Nearest neighbors (KNN) classifier, for example 100 times down-sampling of a negative sample record;
   a random forest classifier, for example where each tree is built using a 2:1 ratio of negative to positive sample records; and
   a gradient boosting machine (GBM) classifier.

Optionally, the performance of each one of the classifiers is estimated using a 10-fold cross validation process where the derivation dataset, referred to herein as a population, is randomly split to ten equal-sized parts. For each part, the following may be performed:

selecting acceptable sets of blood test results from 90% of population not in the respective part;
   training a classifier according to the selected sets of blood test results;
   selecting sets of blood test results from a 10% of population in the respective part; and
   using the classifier on the selected sets of blood test results from the 10% of population.

Now, as shown at 105, the classifier(s) are outputted, optionally as a module that allows classifying target individuals, for example by the interface unit 206. Optionally, different classifiers are defined for individuals having different demographic characteristics, for example one classifier for men and another for women. In another example one classifier is used for smokers and another for non smokers.

Optionally, the classifiers allow evaluating lung cancer by combining the set of current blood test results with smoking history. The set of current blood test results includes some or more of the following blood tests: eosinophil count; eosinophil percentage; neutrophil count; neutrophil percentage; monocyte count; monocyte percentage; basophil count; basophil percentage; lymphocyte counts; lymphocyte percentage; and white blood cell count (WBC); or at least one result of the following red blood cell count (RBC); red blood cell distribution width (RDW); mean cell volume (MCV); mean cell hemoglobin concentration (MCHC); Hematocrit (HCT); Hemoglobin (HGB); and mean cell hemoglobin (MCH); or at least one result of Platelets count; and mean platelet volume (MPV).

Optionally, the lung cancer risk is evaluated by result of at least 2 of the above specified blood test groups.

Optionally, the lung cancer risk is evaluated by classifying biochemistry blood test results of the target individual. In such embodiments, the classifiers are generated according to an analysis of historical biochemistry blood test results of the plurality of individuals, for example as described above. The biochemistry blood test results may include results of any of the above biochemistry tests, includes for example the following blood tests: Albumin, Calcium, Chloride, Cholesterol, Creatinine, high density lipoprotein (HDL), low density lipoprotein (LDL), Potassium, Sodium, Triglycerides, Urea, and/or Uric Acid.

Optionally, the lung cancer risk is evaluated by classifying demographic characteristics of the target individual. In such embodiments, the classifiers are generated according to an analysis of demographic characteristics of the plurality of individuals.

Optionally, both the current blood test results of the target individual and the historical blood test results of sampled individuals are used for generating expended sets of features which include manipulated and/or weighted values. Optionally, each expended set of features is based on the demographic characteristics of a respective individual, for example as described below.

Optionally, the one or more classifiers are adapted to one or more demographic characteristics of the target individual. Optionally, the classifiers are selected to match one or more demographic characteristics of the target individual. In such embodiments, different classifiers may be used for women and men and/or for different age groups.

According to some embodiments of the present invention, there are provided methods and systems of generating one or more classifiers for lung risk evaluation. The methods and systems are based on analysis of a plurality of historical blood test results of each of another of a plurality of sampled individuals and generating accordingly a dataset having a plurality of sets of features each generated according to respective historical blood test results. The dataset is then used to generate and output one or more classifiers, such as K-Nearest neighbors (KNN) classifiers, random forest classifiers, and weighted linear regression classifiers, for example as described above. The classifiers may be provided as modules for execution on client terminals or used as an online service for evaluating lung cancer risk of target individuals based on their current blood test results.

Classifiers are optionally generated as recited in International Patent Application No. PCT/IL2013/050368 filed on May 2, 2013, which is incorporated herein by reference.

The following table summarizes the performances of the different classifiers, each generated according to an analysis of a plurality of respective historical blood test results of a plurality of sampled individuals where the blood test results include data from one or two groups, according to some embodiments of the present invention:

|  | Men 0-30 | | Men 90-180 | | Women 0-30 | | Women 90-180 | |
| --- | --- | --- | --- | --- | --- | --- | --- | --- |
|  | AUC | Sens@95 | AUC | Sens@95 | AUC | Sens@95 | AUC | Sens@95 |
| Optimal (all 4 group parameters) | 0.883 | 56 | 0.832 | 39 | 0.807 | 44 | 0.783 | 33 |
| Only Smx | 0.764 | 29 | 0.755 | 21 | 0.706 | 23 | 0.733 | 21 |
| Only White | 0.837 | 39 | 0.788 | 28 | 0.778 | 30 | 0.737 | 25 |
| Only Red | 0.771 | 29 | 0.789 | 26 | 0.715 | 26 | 0.729 | 22 |
| Only Plts | 0.813 | 39 | 0.748 | 27 | 0.696 | 27 | 0.679 | 12 |
| Smx + White | 0.857 | 46 | 0.810 | 35 | 0.803 | 37 | 0.765 | 28 |
| Smx + Red | 0.814 | 36 | 0.808 | 34 | 0.745 | 33 | 0.764 | 23 |
| Smx + Plts | 0.845 | 42 | 0.787 | 28 | 0.735 | 34 | 0.735 | 22 |

|  | Men 0-30 | | Men 90-180 | | Women 0-30 | | Women 90-180 | |
|---|---|---|---|---|---|---|---|---|
|  | AUC | Sens@95 | AUC | Sens@95 | AUC | Sens@95 | AUC | Sens@95 |
| White + Red | 0.857 | 43 | 0.816 | 36 | 0.793 | 35 | 0.762 | 33 |
| White + Plts | 0.862 | 46 | 0.800 | 30 | 0.788 | 38 | 0.747 | 25 |
| Red + Plts | 0.870 | 47 | 0.807 | 34 | 0.796 | 39 | 0.754 | 29 |

Classifier(s) are generated according to an analysis of a plurality of respective historical blood test results of a plurality of sampled individuals where the blood test results include at least one of:
1) White cells test results, for brevity referred to as White and includes at least one of neutrophils count, basophils count, eosinophils count, lymphocytes count, monocytes count, WBC count, neutrophils percentage, basophils percentage, eosinophils percentage, lymphocytes percentage, monocytes percentage;
2) Platelets cells test results, for brevity referred to as Plts and includes count and/or MPV;
3) Biochemistry test results is selected from a group consisting of Erythrocyte Sedimentation Rate (ESR), Glucose, Urea, Blood Urea Nitrogen (BUN), Creatinine, Sodium, Potassium, Chloride, Calcium, Phosphorus, Uric Acid, Bilirubin Total, Lactate Dehydrogenase (LDH), glutamic oxaloacetic transaminase (GOT), Serum glutamic oxaloacetic transaminase (SGOT), and Glutamate Oxaloacetate, Aspartate transaminase (AST), Aspartate Aminotransferase, glutamate pirovate transaminase (GPT) Serum glutamate pirovate transaminase (SGPT), alanine aminotransferase (ALT), Alkaline Phosphatase (Alk Phos/ALP), gamma glutamyl transpeptidase (GGT), Albumin, CK (Creatine Kinase), Iron, HbA1, B12, Vitamin D, G-6-PD, Lithium, Folic Acid, CRP (C reactive protein), low-density lipoprotein (LDL), high-density lipoprotein (HDL), Triglycerides, Total cholesterol, Amylase, PT (Prothrombin Time), Partial Thromboplastin Time (PTT), Activated Partial Thromboplastin Time (APPT), (International Normalized Ratio (INR), Fibrinogen, Cytidine triphosphate (CPT), Ferritin, glomerular filtration rate (GFR), transferrin, Total iron-binding capacity (TIBC), Unsaturated iron-binding capacity (UIBC).
4) red cells test results, for brevity referred to Red and includes at least one of the following parameters RBC, RDW, MCV, MCHC, Hematocrit, Hemoglobin and MCH.

For example, classifiers are based only on White or Plts. It should be noted that a classifier based on only one of White or Plts yields better outcome than a classifier based on Smx only (see table above). This is not trivial as smoking history is well documented as being correlated to lung cancer.

Optionally, classifiers are based only on 2 of the above group parameters, for example Smx and White, Smx and Plts, Smx and Red, Red and White, Plts and White, and Plts and Red.

Classifier(s) are generated according to an analysis of age and/or gender of each individual.

Classifier(s) generate classifications, also referred to as predictions. The classifications are optionally collected to measure performance of each classifier. For example, the measures of performance are selected according to a receiving operating characteristic (ROC) curve. Optionally, specificity at different (5%, 10%, 20%, 50%, and 70%) sensitivity (recall) values are used for identifying the measures. The performances of the different exemplary classifiers are summarized in the tables which respectively have different area under curve (AUC).

Optionally, each of the plurality of sampled individuals in the individual records includes past value(s) as well as the current value(s) of each of a plurality of blood count parameter(s). Exemplary data in such embodiments may be: AUC=0.94 [0.93, 0.96], OR at sensitivity (SENS 10%) SENS10=438 [123, 626], SENS at false positive ratio (FPR 10)=85.4% [80.7, 89.8], SENS at FPR1=41.8% [34.9, 50.5]. Exemplary data herein below is supported by optimal performance as given by records of medical tests from a Memorial Healthcare System (MHS) of a time-window of 0-30 days, of patients at the age group of 50-75. The records are selected according to sensitivity at FPR of 10%.

Optionally, each of the plurality of sampled individuals in the individual records includes past value(s) as well as the current value(s) of each of a plurality of white blood count parameter(s). Exemplary data in such embodiments may be: AUC=0.94 [0.92, 0.95], OR at SENS10=260 [87, 624], SENS at FPR10=79.4% [74.7, 84.0], SENS at FPR1=38.0% [30.6, 45.4].

Optionally, each of the plurality of sampled individuals in the individual records includes past value(s) as well as the current value(s) of each of a plurality of red blood count parameter(s). Exemplary data in such embodiments may be: AUC=0.88 [0.86, 0.90], OR at SENS10=88 [36, 208], SENS at FPR10=64.1% [58.8, 70.0], SENS at FPR1=27.4% [20.7, 33.9].

Optionally, each of the plurality of sampled individuals in the individual records includes past value(s) as well as the current value(s) of each of a plurality of platelets count parameter(s). Exemplary data in such embodiments may be: AUC=0.91 [0.89, 0.92], OR at SENS10=149 [41, 614], SENS at FPR10=72.9% [66.9, 78.3], SENS at FPR1=35.4% [28.1, 42.3].

Optionally, each of the plurality of sampled individuals in the individual records includes past value(s) as well as the current value(s) of each of platelets information. Exemplary data in such embodiments may be: AUC=0.94 [0.92, 0.95], OR at SENS10=232 [76, 621], SENS at FPR10=80.7% [75.6, 85.2], SENS at FPR1=37.7% [31.2, 44.7].

Optionally, each of the plurality of sampled individuals in the individual records includes past value(s) as well as the current value(s) of each of white blood counts and any parameter of the red blood counts. Exemplary data in such embodiments may be: AUC=0.93 [0.92, 0.95], OR at SENS10=326 [77, 625], SENS at FPR10=80.1% [75.0, 84.8], SENS at FPR1=38.2% [32.3, 45.2].

Optionally, each of the plurality of sampled individuals in the individual records includes past value(s) as well as the current value(s) of any parameter of the white blood counts and any parameter of the platelets information or any parameter of the white line counts and any biochemistry parameter.

Optionally, each of the plurality of sampled individuals in the individual records includes past value(s) as well as the current value(s) of any parameter of the red blood counts and any parameter of the platelets information. In such embodiments, AUC=0.92 [0.90, 0.93], OR at SENS10=194 [57, 619], SENS at FPR10=76.6% [71.1, 81.6], SENS at FPR1=35.2% [27.4, 42.2].

Optionally, each of the plurality of sampled individuals in the individual records includes past value(s) as well as the current value(s) of the platelets information and any biochemistry parameter.

Optionally, each of the plurality of sampled individuals in the individual records includes past value(s) as well as the current value(s) of the red blood counts and any biochemistry parameter.

Optionally, each of the plurality of sampled individuals in the individual records includes past value(s) as well as the current value(s) of Neutrophils counts. In such embodiments, AUC=0.90 [0.89, 0.92], OR at SENS10=44 [23, 89], SENS at FPR10=69.2% [62.9, 74.8], SENS at FPR1=22.2% [16.9, 28.6].

Optionally, each of the plurality of sampled individuals in the individual records includes past value(s) as well as the current value(s) of Hematocrit. In such embodiments, AUC=0.88 [0.86, 0.90], OR at SENS10=88 [36, 208], SENS at FPR10=64.1% [58.8, 70.0], SENS at FPR1=27.4% [20.7, 33.9].

Optionally, each of the plurality of sampled individuals in the individual records includes past value(s) as well as the current value(s) of Platelets count. Exemplary data in such embodiments may be: AUC=0.91 [0.89, 0.92], OR at SENS10=149 [41, 614], SENS at FPR10=72.9% [66.9, 78.3], SENS at FPR1=35.4% [28.1, 42.3].

Optionally, each of the plurality of sampled individuals in the individual records includes past value(s) as well as the current value(s) of white line counts and any parameter of the red line counts, and any parameter of the platelets information. Exemplary data in such embodiments may be: AUC=0.94 [0.93, 0.96], OR at SENS10=438 [123, 626], SENS at FPR10=85.4% [80.7, 89.8], SENS at FPR1=41.8% [34.9, 50.5].

Optionally, each of the plurality of sampled individuals in the individual records includes past value(s) as well as the current value(s) of any parameter of the white line counts, and any parameter of the red line counts, and any parameter of the platelets information and any biochemistry parameter.

Optionally, each of the plurality of sampled individuals in the individual records includes past value(s) as well as the current value(s) of any parameter from CBC or biochemistry and family history of lung cancer, any parameter of the white blood counts and family history of lung cancer, any information of the red blood count and family history of lung cancer, any parameter from CBC or biochemistry and body mass index (BMI), any parameter of the white blood counts and BMI, any information of the red blood count and BMI. any parameter from CBC or biochemistry and comorbidity (e.g. COPD), any parameter of the white blood counts and comorbidity, any information of the red blood count and comorbidity, any parameter from CBC or biochemistry and socio-economic indicators (e.g. Education level) any parameter of the white blood counts and socio-economic indicators, and/or any information of the red blood count and socio-economic indicators.

It is expected that during the life of a patent maturing from this application many relevant systems and methods will be developed and the scope of the term a processor, a display, and user interface is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computerized method of training a classifier for providing an evaluation of lung cancer risk in response to an indication of current blood tests results of a target individual, comprising:
generating a derivation dataset from a plurality of sample records of each of another of a plurality of sample individuals, each respective sample record of a respective sample individual including a plurality of historical blood test results and smoking history, wherein each of the plurality of sample records is associated with a label indicative of whether the respective sample individual is positive or negative for lung cancer,
the derivation dataset including a plurality of sets of combinations of processed features, each set of combination of processed features generated from each one of the plurality of sample records, each set of combination of processed features including unprocessed features comprising smoking history of the sample individuals and 1-20 historical blood test results including results of actual blood test values selected from the following group of blood tests consisting of: white blood cell (WBC) count, platelets blood test results including at least one of platelets count and mean platelet volume (MPV), biochemistry and red cell distribution width (RDW);
iteratively filtering the derivation dataset to remove outlying features; and
training at least one classifier on the derivation dataset.

2. The computerized method of claim 1, wherein each set of combination of processed features includes actual blood test values that include each one of WBC count, platelets blood test results including at least one of platelets count and MPV, and RDW.

3. The computerized method of claim 1, further comprising expanding each set of combination of processed features of the derivation dataset, by computing each one of a plurality of expanded features from at least two unprocessed features, wherein each set of combination of features stored in the derivation dataset includes unprocessed features and expanded features.

4. The computerized method of claim 3, wherein expanding comprises including manipulated and/or weighted values.

5. The computerized method of claim 1, wherein each set of combination of processed features are weighted according to a date of the respective plurality of historical blood test results.

6. The computerized method of claim 1, wherein each set of combination of processed features includes actual blood test values selected from each of the following groups of blood tests:
(i) neutrophils count, basophils count, eosinophils count, lymphocytes count, monocytes count, neutrophils percentage, basophils percentage, eosinophils percentage, lymphocytes percentage, and monocytes percentage, and
(ii) red blood cells (RBC), blood tests hemoglobin (MCH), mean cell volume (MCV), mean corpuscular hemoglobin concentration (MCHC), Hematocrit, and Hemoglobin.

7. The computerized method of claim 1, wherein said Biochemistry test results is selected from a group consisting of Erythrocyte Sedimentation Rate (ESR), Glucose, Urea, Blood Urea Nitrogen (BUN), Creatinine, Sodium, Potassium, Chloride, Calcium, Phosphorus, Uric Acid, Bilirubin Total, Lactate Dehydrogenase (LDH), glutamic oxaloacetic transaminase (GOT), Serum glutamic oxaloacetic transaminase (SGOT), and Glutamate Oxaloacetate, Aspartate transaminase (AST), Aspartate Aminotransferase, glutamate pirovate transaminase (GPT) Serum glutamate pirovate transaminase (SGPT), alanine aminotransferase (ALT), Alkaline Phosphatase (Alk Phos/ALP), gamma glutamyl transpeptidase (GGT), Albumin, CK (Creatine Kinase), Iron, HbA1, B12, Vitamin D, G-6-PD, Lithium, Folic Acid, CRP (C reactive protein), low-density lipoprotein (LDL), high-density lipoprotein (HDL), Triglycerides, Total cholesterol, Amylase, PT (Prothrombin Time), Partial Thromboplastin Time (PTT), Activated Partial Thromboplastin Time (APPT), (International Normalized Ratio (INR), Fibrinogen, Cytidine triphosphate (CPT), Ferritin, glomerular filtration rate (GFR), transferrin, Total iron-binding capacity (TIBC), Unsaturated iron-binding capacity (UIBC).

8. The computerized method of claim 1, wherein each set of combination of processed features includes at least one demographic parameter of a respective sample individuals.

9. The computerized method of claim 8, wherein said at least one demographic parameter is a member of a group consisting of gender, age, residential zone, race and socio-economic characteristic.

10. The computerized method of claim 1, wherein each set of combination of processed includes at least one of: (i) results of both neutrophils percentage/count and lymphocytes percentage/count, (ii) results of Platelets hematocrit (PCT), (iii) results of both HGB and HCT, or (iv) at least one of the following blood tests: eosinophils count; neutrophils percentage; monocytes percentage; eosinophils percentage; basophils percentage; and neutrophils count; monocytes count.

11. The computerized method of claim 1, wherein said at least one classifier comprises a member of a group consisting of: a weighted linear regression classifier, a K-Nearest neighbors (KNN) classifier, and a random forest classifier.

12. The computerized method of claim 1, wherein the at least one classifier comprises a gradient boosting machine (GBM).

13. The method of claim 1, wherein the combination of features includes at least 10 blood test results.

14. The method of claim 1, wherein less than 20 blood test results comprises less than 15 blood test results.

15. The method of claim 1, wherein less than 20 blood test results comprises less than 10 blood test results.

16. The method of claim 1, wherein the combination of features based on said plurality of historical and current blood test results comprises a plurality of historical blood test results for a same blood test.

17. A computerized method of using at least one classifier for providing an evaluation of lung cancer risk in response to an indication of current blood tests results of a target individual, comprising:
generating, by a computing system associated with a database storing the at least one classifier, a combination of features based on a plurality of current blood test results calculated based on an analysis of a blood collected from a target individual and a smoking history of the target individual, wherein the combination of features include unprocessed features comprising smoking history of the sample individuals and less than 20 historical blood test results including results of actual blood test values selected from the following blood tests: WBC count, platelets blood test results including at least one of platelets count and mean platelet volume (MPV), and red cell distribution width (RDW);
using a hardware processor of the computing system feeding said combination of features into said at least one classifier; and
outputting by said at least one classifier, a numerical value indicative of a lung cancer risk of said target individual,
wherein the at least one classifier is trained on a derivation dataset generated from a plurality of sample records of each of another of a plurality of sample individuals, each respective sample record of a respective sample individual including a plurality of historical blood test results and smoking history, wherein each of the plurality of sample records is associated with a label indicative of whether the respective sample individual is positive or negative for lung cancer,
the derivation dataset including a plurality of sets of combinations of processed features, each set of combination of processed features generated from each one of the plurality of sample records, each set of combination of processed features including unprocessed features comprising smoking history of the sample individuals and 1-20 historical blood test results including results of actual blood test values selected from the following group of blood tests consisting of: WBC count, platelets blood test results including at least one of platelets count and mean platelet volume (MPV), biochemistry and red cell distribution width (RDW),
wherein the derivation dataset is iteratively filtered to remove outlying features.

18. The method of claim 17, wherein outputting by the at least one classifier comprises outputting by the at least one classifier, at least one of: a first classification indicative of high risk for lung cancer, and a second classification indicative of low risk for lung cancer, and when the target individual is identified at high risk for lung cancer at the pre-screening stage, further comprises screening the target individual for lung cancer using Low Dose Computed Tomography (LDCT).

19. A computing device for training a classifier for providing an evaluation of lung cancer risk in response to an indication of current blood tests results of a target individual, comprising:
at least one hardware processor executing a code for:
generating a derivation dataset from a plurality of sample records of each of another of a plurality of sample individuals, each respective sample record of a respective sample individual including a plurality of historical blood test results and smoking history, wherein each of the plurality of sample records is associated with a label indicative of whether the respective sample individual is positive or negative for lung cancer,
the derivation dataset including a plurality of sets of combinations of processed features, each set of combination of processed features generated from each one of the plurality of sample records, each set of combination of processed features including unprocessed features comprising smoking history of the sample individuals and 1-20 historical blood test results including results of actual blood test values selected from the following group of blood tests consisting of: WBC count, platelets blood test results including at least one of platelets count and mean platelet volume (MPV), biochemistry and red cell distribution width (RDW);
iteratively filtering the derivation dataset to remove outlying features; and
training at least one classifier on the derivation dataset.

20. The method of claim 1, wherein the 1-20 historical blood test results include a combination of at least two blood test results including results of actual blood test values selected from the group consisting of WBC count, platelets blood test results including at least one of platelets count and mean platelet volume (MPV), biochemistry and red cell distribution width (RDW).

21. The method of claim 1, wherein each respective sample record of a respective sample individual further includes at least one of weight of the respective sample individual and body mass index (BMI) of the respective sample individual, wherein each set of combination of processed features further includes unprocessed features comprising at least one of the weight and BMI of the sample individual.

22. The method of claim 1, wherein 1-20 blood tests comprises 5-20 blood tests.

* * * * *